United States Patent [19]

Stevens et al.

[11] Patent Number: 5,681,858
[45] Date of Patent: Oct. 28, 1997

[54] CYCLOALKYL HYDROXYUREAS

[75] Inventors: Rodney William Stevens; Takashi Mano, both of Handa; Yoshiyuki Okumura, Chita; Masami Nakane, Nagoya, all of Japan

[73] Assignee: Pfizer Inc., New York, N.Y.

[21] Appl. No.: 525,748

[22] PCT Filed: Apr. 5, 1994

[86] PCT No.: PCT/JP94/00567

§ 371 Date: Oct. 3, 1995

§ 102(e) Date: Oct. 3, 1995

[87] PCT Pub. No.: WO94/22814

PCT Pub. Date: Oct. 13, 1994

[30] Foreign Application Priority Data

Apr. 7, 1993 [JP] Japan ............... 5-080952

[51] Int. Cl.[6] .................. A61K 31/17; C07C 275/24; C07C 273/02
[52] U.S. Cl. .................. 514/595; 564/47; 564/52; 564/56; 564/57; 564/61; 564/62
[58] Field of Search .................. 514/595; 564/47, 564/52, 57, 56, 61, 62

[56] References Cited

U.S. PATENT DOCUMENTS 5,476,873 12/1995 Brooks et al. ............... 514/595

FOREIGN PATENT DOCUMENTS 0436199 7/1991 European Pat. Off. .
9201682 2/1992 WIPO .
9209566 6/1992 WIPO .
9209567 6/1992 WIPO .

Primary Examiner—Shailendra Kumar
Attorney, Agent, or Firm—Peter C. Richardson; Gregg C. Benson; A. Dean Olson

[57] ABSTRACT

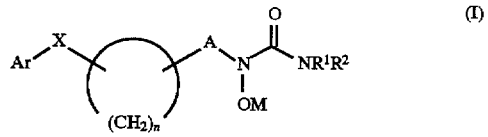

The present invention provides a novel N-hydroxyurea compound of chemical formula (I) wherein $R^1$ and $R^2$ are each independently hydrogen or $C_1$–$C_4$ alkyl; Ar is phenyl or mono-, di- or trisubstituted phenyl; A is a valence bond or a $C_1$–$C_6$ alkylene chain, optionally having one double bond or one triple bond in the chain, and optionally having one or more $C_1$–$C_4$ alkyl groups attached to the chain: X is oxygen or sulfur, n is an integer of 3 to 6; M is hydrogen, pharmaceutically acceptable cation or a metabolically cleavable group: and X and A may be attached at any available position on the ring. These compounds are useful for treatment or alleviation of inflammatory diseases, allergy and cardiovascular diseases in mammals and as the active ingredient in pharmaceutical compositions for treating such conditions.

13 Claims, No Drawings

CYCLOALKYL HYDROXYUREAS

This application is a 371 of PCT/JP94/00567 filed Apr. 5, 1994.

TECHNICAL FIELD

This invention relates to novel cycloalkylhydroxyureas. The compounds of the present invention inhibit the action of the lipoxygenase enzyme and are useful in the treatment or alleviation of inflammatory diseases, allergy and cardiovascular diseases in mammals, especially human subjects. This invention also relates to pharmaceutical compositions comprising such compounds.

BACKGROUND ART

Arachidonic acid is known to be the biological precursor of several groups of biologically active endogenous metabolites. The first step in the metabolism of arachidonic acid is its release from membrane phospholipids, via the action of phospholipase A2. Arachidonic acid is then metabolized either by cyclooxygenase to produce prostaglandins including prostacyclin, and thromboxanes or by lipoxygenase to generate hydroperoxy fatty acids which may be further converted to the leukotrienes.

The leukotrienes are extremely potent substances which elicit a wide variety of biological effects, often in the nanomolar to picomolar concentration range. The peptido-leukotrienes ($LTC_4$, $LTD_4$, $LTE_4$) are important bronchoconstrictors and vasoconstrictors, and also cause plasma extravasation by increasing capillary permeability. $LTB_4$ is a potent chemotactic agent, enhancing the influx of leukocytes and inducing their subsequent degranulation at the site of inflammation. A pathophysiological role for leukotriene has been implicated in a number of human disease states including asthma, rheumatoid arthritis and gout, psoriasis, adult respiratory distress syndrome, inflammatory bowel diseases (e.g. Crohn's disease), endotoxin shock, and ischemia-induced myocardial injury. Any agent that inhibits the action of lipoxygenases is expected to be of considerable therapeutic value for the treatment of acute and chronic inflammatory conditions.

Compounds of similar structure to the compounds of the present invention are disclosed in the following publications: WO92/01682, WO92/09566 and WO92/09567.

BRIEF DISCLOSURE OF THE INVENTION

The present invention provides novel cycloalkyl-N-hydroxyurea compounds of the following chemical formula (I):

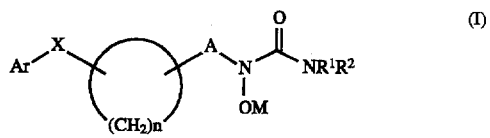

wherein $R^1$ and $R^2$ are each independently hydrogen or $C_1$–$C_4$ alkyl;

Ar is phenyl or mono-, di- or trisubstituted phenyl;

A is a valence bond or a $C_1$–$C_6$ alkylene chain, optionally having one double bond or one triple bond in the chain, and optionally having one or more $C_1$–$C_4$ alkyl groups attached to the chain;

X is oxygen or sulfur;

n is an integer of 3 to 6;

M is hydrogen, pharmaceutically acceptable cation or a metabolically clearable group; and X and A may be attached at any available position on the ring.

Preferably, when Ar is mono-, di- or trisubstituted phenyl, the substituents are independently selected from the group consisting of halogen, $C_1$–$C_4$ alkyl, $C_1$–$C_4$ alkoxy, halosubstituted ($C_1$–$C_6$) alkyl and halosubstituted ($C_1$–$C_6$) alkoxy. Particularly preferred groups for Ar are phenyl and monohalo phenyl, especially phenyl and 4-fluorophenyl.

Preferably M is hydrogen or a pharmaceutically acceptable cation.

A preferred group of the compounds of this invention consists of the compounds of formula (I), wherein $R^1$ and $R^2$ are each hydrogen; Ar is mono-, di- or trisubstituted phenyl, wherein the substituents are independently selected from the group consisting of halogen, $C_1$–$C_4$ alkyl, $C_1$–$C_4$ alkoxy, halosubstituted ($C_1$–$C_6$) alkyl and halosubstituted ($C_1$–$C_6$) alkoxy; X is oxygen; n is 4 or 5; and M is hydrogen or a pharmaceutically acceptable cation. Within this preferred group, particularly preferred compounds are those in which A is a valence bond, —CH($CH_3$)— or —C≡C—CH($CH_3$)—.

Preferred compounds of the present invention are:

(+)-N-[4-cis-3-(4-fluorophenoxy)cyclobutyl}-3-butyn-2-yl-N-hydroxyurea;

(−)-N-[4-cis-3-(4-fluorophenoxy)cyclobutyl}-3-butyn-2-yl-N-hydroxyurea;

(+)-N-[4-trans-3-(4-fluorophenoxy)cyclobutyl}-3-butyn-2-yl-N-hydroxyurea;

(−)-N-[4-trans-3-(4-fluorophenoxy)cyclobutyl}-3-butyn-2-yl-N-hydroxyurea; N-hydroxy-N-(1S,3S)-3-phenoxycyclopentylurea;

(+)-N-[4-{cis-3-(4-chlorophenoxy)cyclobutyl}-3-butyn-2-yl]-N-hydroxyurea:

(−)-N-[4-{cis-3-(4-chlorophenoxy)cyclobutyl}-3-butyn-2-yl]-N-hydroxyurea;

(+)-N-[4-{cis-3-(2-chloro-4-fluorophenoxy)cyclobutyl}-3-butyn-2-yl]-N-hydroxyurea;

(−)-N-[4-{cis-3-(2-chloro-4-fluorophenoxy)cyclobutyl}-3-butyn-2-yl]-N-hydroxyurea;

(+)-N-[4-{cis-3-(4-fluoro-2-methylphenoxy)cyclobutyl}-3-butyn-2-yl]-N-hydroxyurea; and (−)-N-[4-{cis-3-(4-fluoro-2-methylphenoxy)cyclobutyl}-3-butyn-2-yl]-N-hydroxyurea.

The compounds of the formula I can inhibit the action of lipoxygenase. Therefore the compounds are useful for treating a medical condition for which a 5-lipoxygenase inhibitor is needed, in a mammalian subject, e.g., a human subject. The compounds are especially useful for treating inflammatory diseases, allergy and cardiovascular diseases. This invention also embraces pharmaceutical compositions which comprise a compound of the formula (I) and a pharmaceutically acceptable carrier, and a method for the treatment of a medical condition for which a 5-lipoxygenase inhibitor is needed, in a mammalian subject.

DETAILED DESCRIPTION OF THE INVENTION

In this specification, the term "alkyl" is used herein to mean straight or branched hydrocarbon chain radicals including, but not limited to, methyl, ethyl, n-propyl, isopropyl, n-butyl, isobutyl, sec-butyl, tert-butyl, and the like;

the term "alkoxy" is used herein to mean —OR (R is alkyl) including, but not limited to, methoxy, ethoxy, propoxy, isopropoxy, n-butoxy, isobutoxy, sec-butoxy, tert-butoxy and the like;

the term "halosubstituted alkyl" refers to an alkyl radical as described above substituted with one or more halogens including, but not limited to, chloromethyl, bromoethyl, trifluoromethyl and the like;

the term "halosubstituted alkoxy" refers to an alkoxy radical as described above substituted with one or more halogens including, but not limited to, chloromethoxy, bromoethoxy, difluoromethoxy, trifluoromethoxy and the like;

the term "pharmaceutically acceptable cation" refers to non-toxic cations, based on alkaline and alkaline earth metals such as sodium, lithium, potassium, calcium and magnesium, and the like, as well as those based on non-toxic ammoniums, quaternary ammoniums, including, but not limited to, ammonium, ethylammonium, diethylammonium, triethylammonium, tetraethylammonium, tetramethylammonium and tetrabutylammonium and the like.

The term "metabolically cleavable group" denotes a group which is cleaved in vivo to yield the parent molecule of the structural formula (I) wherein M is hydrogen. Examples of metabolically clearable groups include —COY, —COOY, —CONH$_2$, —CONYY', —CH$_2$OY, —CH(Y') OY, —CH$_2$OCOY, —CH$_2$OCO$_2$Y, —CH(Y')OCO$_2$Y radicals where Y and Y' are each independently selected from ($C_1$–$C_4$) alkyl, phenyl or substituted phenyl wherein the substituent is selected from one or more of $C_1$–$C_4$ alkyl, halogen, hydroxy or $C_1$–$C_4$ alkoxy. Specific examples of representative metabolically cleavable groups include, but are not limited to, acetyl, ethoxycarbonyl, benzoyl and methoxymethyl groups.

It is obvious to those skilled in the art that if the group A contains a double bond or a triple bond, the double or triple bond is not directly linked to the nitrogen atom attached to (OM).

The novel cycloalkylhydroxyureas of the present invention in formula (I) are described in a planar structure, but when they possess one asymmetric center, they are capable of occurring as optical isomers. When they have at least two asymmetric carbon atoms, they can additionally exist as diastereomers. The present invention includes all such forms within its scope. For instance, the individual optical isomers and the diastereomers can be obtained by methods well known to those skilled in the art, e.g., by separation of mixtures, asymmetric synthesis and the like. Hence, when those skilled in the art use the compounds of this invention, they may choose any desired isomers, such as optical isomers and diastereomers, or mixtures thereof, from among the objective compounds of the present invention according to their application purpose.

The pharmaceutical compositions of the present invention comprise a compound of formula (I) as an active ingredient and may also contain a pharmaceutically acceptable carrier.

The novel hydroxyureas of formula (I) may be prepared by a number of synthetic methods which are well known by those skilled in the art.

In one embodiment, compounds of the formula (I) are prepared according to the reaction step outlined in Scheme 1.

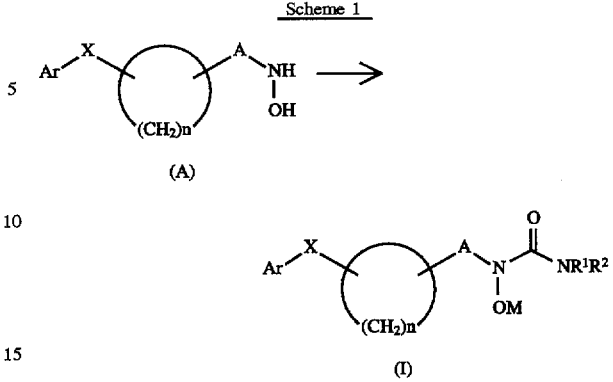

wherein M is hydrogen and $R^1$ and $R^2$ are each independently hydrogen or $C_1$–$C_4$alkyl; and Ar, A, X and n are as defined previously.

In the reaction step in scheme 1, the compounds (I) are obtained by treating the requisite hydroxylamine (A) with a trialkylsilyl isocyanate, such as trimethylsilyl isocyanate, or an alkyl isocyanate of the formula $R^1$—N=C=O in a reaction-inert solvent. Suitable solvents which do not react with reactants and/or products are, for example, tetrahydrofuran (THF), dioxane, methylene chloride or benzene. Reaction temperatures are usually in the range of from room temperature to the reflux temperature of the solvent, e.g., 15° to 100° C. but if necessary, temperatures lower or higher can be adopted. The reaction is easily monitored by thin-layer chromatography (TLC) techniques and the reaction time is in general from a few minutes to several hours.

An alternative procedure for Scheme 1 employs treatment of (A) with gaseous hydrogen chloride in a reaction-inert solvent such as benzene or toluene and then subsequent treatment with phosgene. Reaction temperatures are usually in the range of room temperature through to boiling point of solvent, e.g., 15° to 100° C., but if necessary, temperatures lower or higher can be adopted. The intermediate chloroformamide is not isolated but subjected to (i.e. in situ) reaction with an appropriate amine (NHR$^1$R$^2$) such as ammonia or methylamine. The reaction is easily monitored by TLC and the reaction time is in general from a few minutes to several hours.

As a modification of this procedure, when $R^1$ and $R^2$ are both hydrogen, the acid addition salt of the hydroxylamine (A) may be reacted with an equimolar amount of an alkali metal cyanate, such as potassium cyanate, in water. The starting material, hydroxylamine (A), may be readily prepared by standard synthetic procedures from corresponding carbonyl compound, i.e. ketone or aldehyde, alcohol compound, or halogen compound. For example, suitable carbonyl compound is converted to its oxime and then reduced to the requisite hydroxylamine (A) with a suitable reducing agent (for example, see R. F. Borch et al, J. Amer. Chem. Soc., 93, 2897, 1971). Reducing agents of choice are sodium cyanoborohydride and borane complexes such as borane-pyridine, borane-triethylamine and borane-dimethylsulfide, however triethylsilane in trifluoroacetic acid (TFA) may also be employed.

Alternately, hydroxylamine (A) can easily be prepared by treating the corresponding alcohol with, for example, N,o-bis(tert-butyloxycarbonyl)hydroxylamine under Mitsunobu-type reaction conditions followed by acid catalyzed hydrolysis (for example, employing TFA or HCl—MeOH solution) of the N,o-protected intermediate (see JP(kokai)45344/

1989). Suitable condensing reagents in the Mitsunobu reaction are for example, diethyl azodicarboxylate and triphenylphosphine. A reaction-inert solvent such as methylene chloride, THF, dimethylformamide or toluene is used. The reaction temperatures are preferably in the range of room temperature to the reflux temperature of the solvent, e.g. 15° to 100° C., but if necessary, temperatures lower or higher can be adopted. The reaction is easily monitored by TLC. The reaction time is in general from a few minutes to several hours.

The aforementioned hydroxylamine (A) may also be prepared from suitable halide compound by reaction with o-protected hydroxylamine and subsequent deprotection (see W. P. Jackson et. al., *Journal of Medicinal Chemistry*, 1988, 31, 499). Preferred o-protected hydroxylamines are, but not limited to, o-tetrahydropyranyl-, o-trimethylsilyl- and o-benzylhydroxylamine.

In another embodiment, compounds of the formula (I) are prepared as illustrated in Scheme 2:

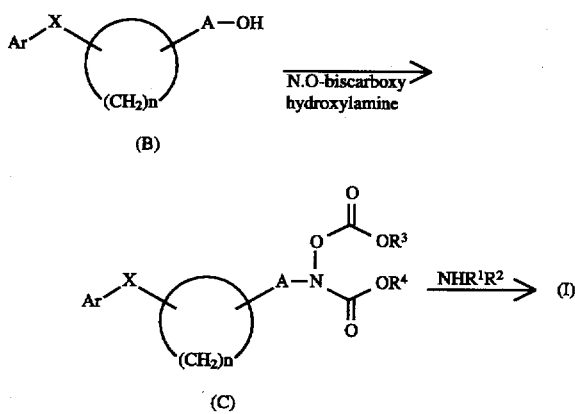

wherein M is hydrogen, $R^3$ is phenyl and $R^4$ is phenyl or $C_1$–$C_4$ alkyl; and $R^1$, $R^2$, Ar, A, X and n are as defined previously.

In scheme 2, the compounds (I) are obtained by treating the alcohol (B) with a N,o-biscarboxyhydroxylamine preferably N,o-bis(phenoxycarbonyl)hydroxylamine, and subsequently converting the resulting product (C) to (I) by treatment with an appropriate amine ($NHR^1R^2$) such as ammonia, methylamine or dimethylamine (A. O. Stewart and D. W. Brooks., *J. Org. Chem.*, 1992, 57, 5020) in the absence of solvent or in a reaction-inert solvent. Suitable condensing reagents for conversion of (B) to (C) are, for example, diethyl azodicarboxylate and triphenylphosphine. Preferred reaction-inert solvents for the condensation reaction are methylene chloride, THF, dimethylformamide and toluene. The condensation reaction temperatures are preferably in the range of room temperature to the reflux temperature of the solvent, but if necessary, temperatures lower or higher can be adopted. The reaction is easily monitored by TLC. The reaction time is in general from a few minutes to several hours. Preferred solvents in the reaction from (C) to (I) are, for example, water, methanol, ethanol, THF and benzene but the reaction can be carried out without any solvent. The range of preferable temperature in the reaction from (C) to (I) is from room temperature to the reflux temperature of the solvent, (e.g., 15°–100° C.), but if necessary, temperatures lower or higher can be adopted. The reaction is easily monitored by TLC. The reaction time is in general from a few minutes to several hours.

When M is a pharmaceutically acceptable cation in formula (I), the compound may be prepared by the well-known method to those skilled in the art. For example, the compound is prepared by reacting an equivalent amount of alkaline, alkaline earth metals and alkoxide, amine or ammonium hydroxide with the compound (I), wherein M is hydrogen, in water or a suitable organic solvent. The salts are obtained by subsequent precipitation and filtration, or by removal of the solvent by evaporation.

When M is metabolically cleavable group, the compound (I) is obtained by treating the compound (I) wherein M is hydrogen with various electrophiles M—Z (Z is Cl, Br etc.) such as acetyl chloride, ethyl bromocarbonate or the like.

The products which are mentioned in the general syntheses are isolated by standard methods and purification can be achieved by conventional means, such as recrystallization and chromatography.

The compounds of this invention inhibit the activity of lipoxygenase enzyme. This inhibition has been demonstrated in vitro by 1) an assay using rat peritoneal cavity resident cells (*Japanese Journal of Inflammation*, 1987, 7, 145–150, "Synthesis of leukotrienes by peritoneal macrophages") and 2) an assay using heparinised human whole blood (*Agents and Actions*, 1987, 21, 393–396), both of which determine the inhibitory effect of said compounds on 5-lipoxygenase metabolism of arachidonic acid. Some preferred compounds were shown to possess low $IC_{50}$ values, in the range of 0.01 to 1 µM, with respect to lipoxygenase activity.

The ability of the compounds of the present invention to inhibit lipoxygenase enzyme makes them useful for controlling the symptoms induced by the endogenous metabolites arising from arachidonic acid in a mammalian subject. The compounds are therefore valuable in the prevention and treatment of such disease states in which the accumulation of arachidonic acid metabolites are the causative factor; e.g. allergic bronchial asthma, skin disorders, rheumatoid arthritis and osteoarthritis. Thus, the compounds of the present invention are of particular use in the treatment or alleviation of inflammatory diseases in a human subject.

For treatment of the various conditions described above, the compounds can be administered to a human subject either alone, or preferably in combination with pharmaceutically acceptable carriers or diluents in a pharmaceutical composition according to standard pharmaceutical practice.

The compounds can be administered to a human subject by various conventional routes of administration including oral, parenteral and by inhalation. When the compounds are administered orally, the dose range will be from about 0.1 to 20 mg/kg of body weight of the subject to be treated per day, preferably from about 0.5 to 10 mg/kg per day in single or divided doses. If parenteral administration is desired, then an effective dose will be from about 0.1 to 1.0 mg/kg of body weight of the subject to be treated per day. In some instances it may be necessary to use dosages outside these limits, since the dosages will necessarily vary according to the age, weight and response of the individual patient as well as the severity of the patient's symptoms and the potency of the particular compound being administered.

For oral administration, the compounds of the invention can be administered, for example, in the form of tablets, powders, lozenges, syrups or capsules or as an aqueous solution or suspension. In the case of tablets for oral use, carriers which are commonly used include lactose and corn starch. Further lubricating agents such as magnesium stearate are commonly added. In the case of capsules, useful diluents are lactose and dried corn starch. When aqueous suspensions are required for oral use, the active ingredient is combined with emulsifying and suspending agents. If desired, certain sweetening and/or flavoring agents can be added. For intramuscular, intraperitoneal, subcutaneous and intravenous use, sterile solutions of the active ingredient are usually prepared and the pH of the solutions should be suitably adjusted and buffered. For intravenous use, the total concentration of solute should be controlled to make the preparation isotonic.

EXAMPLES

The present invention is illustrated by the following examples. However, it should be understood that the invention is not limited to the specific details of these examples. Melting points were taken with a Yanako micro melting point apparatus and are uncorrected. IR spectra were obtained on a Shimadzu IR-470 infrared spectrophotometer. Optical rotations were obtained on a JASCO DIP-370 polarimeter. All NMR spectra were measured in $CDCl_3$ by a JEOL NMR spectrometer (JNM-GX270, 270 MHz) unless otherwise indicated and peak positions are expressed in pans per million (ppm) down field from tetramethylsilane. The peak shapes are denoted as follows: s, singlet; d, doublet; t, triplet; q, quartet; m, multiplet; br, broad.

Example 1

Preparation of N-[4-{cis-3-(4-fluorophenoxy) cyclopentyl}-3-butyn-2-yl]-N-hydroxyurea.

(i)3-(1,3-Dithian-2-yl)cyclopentanol.

To a stirred solution of 3-(1,3-dithian-2-yl) cyclopentanone (*J. Chem. Soc., Chem. Commun.*, 1979, 100) (42.0 g, 208 mmol) in methanol (200 ml) cooled to 0° C. was added, portionwise, sodium borohydride (8.00 g, 210 mmol). After completion of addition, the reaction mixture was allowed to warm to room temperature and stirred a further 3 h. The majority of methanol was removed under reduced pressure, water (100 ml) added and the residue was extracted with ethyl acetate (200 ml). The organic phase was washed with brine (200 ml), dried ($MgSO_4$) and concentrated in vacuo to afford 43.5 g (quant.) of title compound as a pale yellow oil: $^1H$ NMR δ4.43–4.28 (m, 1H), 4.19–4.00 (m, 1H), 2.90–2.81 (m, 4H), 2.30–1.42 (m, 10H).

(ii)1-(1,3-Dithian-2-yl)-3-(4-fluorophenoxy) cyclopentane.

To a stirred solution of 3-(1,3-dithian-2-yl)cyclopentanol (40.0 g, 196 mmol), 4-fluorophenol (23.5 g, 210 mmol) and triphenylphosphine (55.1 g, 210 mmol) in dry THF (400 ml) cooled to 0° C. was added dropwise a solution of diethyl azodicarboxylate (43.5 g, 250 mmol) in dry THF (100 ml). The mixture was stirred for 1 h at room temperature and volatiles removed under reduced pressure. Chromatographic purification of the residue {$SiO_2$, 1700 g; hexane/ethyl acetate (20:1)} provided 45.5 g (78%) of title compound as a colorless oil: $^1H$ NMR δ6.98–6.90 (m, 2H), 6.83–6.75 (m, 2H), 4.78–4.65 (m, 1H), 4.06 (d, J=7.7 Hz, 1H), 2.97–2.80 (m, 4H), 2.35–1.72 (m, 8H), 1.70–1.55 (m, 1H).

(iii) cis-3-(4-Fluorophenoxy) cyclopentanecarbaldehyde and trans-3-(4-fluorophenoxy)cyclopentanecarbaldehyde.

To a stirred solution of 1-(1,3-dithian-2-yl)-3-(4-fluorophenoxy)cyclopentane (10.0 g, 33.5 mmol) in 75% aqueous acetonitrile (300 ml) was added eerie ammonium nitrate (*J. Chem Soc., Chem. Commun.*, 1977, 680) (74.0 g, 135 mmol) at room temperature. The reaction mixture was stirred for 0.5 h at the same temperature, diluted with water (500 ml) and then extracted with ether (500 ml). The ether phase was washed with brine (300 ml), dried ($MgSO_4$) and concentrated in vacuo. Purification by flash column chromatography {$SiO_2$, 250 g; hexane/ethyl acetate (10:1)} gave 1.28 g (20%) of cis-3-(4-fluorophenoxy) cyclopentanecarbaldehyde (Rf=0.2), 2.35 g (37%) of trans-3-(4-fluorophenoxy)cyclopentanecarbaldehyde (Rf=0.25) and 1.01 g (17%) of cis/trans mixture, respectively, as colorless oils: cis-3-(4-fluorophenoxy) cyclopentanecarbaldehyde; $^1H$ NMR δ9.66 (s, 1H), 7.06–6.90 (m, 2H), 6.86–6.75 (m, 2H), 4.87–4.73 (m, 1H), 2.91–2.73 (m, 1H), 2.40–1.80 (m, 6H): trans-3-(4-fluorophenoxy)cyclopentanecarbaldehyde; $^1H$ NMR δ9.71 (s, 1H), 7.05–6.91 (m, 2H), 6.90–6.75 (m, 2H), 4.87–4.72 (m, 1H), 3.25–3.01 (m, 1H), 2.32–1.79 (m, 6H).

(iv) 1,1-Dibromo-2-{cis-3-(4-fluorophenoxy) cyclopentyl}ethene.

To a mixture of zinc dust (4.10 g, 63 mmol) and triphenylphosphine (16.5 g, 63 mmol) in $CH_2Cl_2$ (100 ml) was added carbon tetrabromide (20.9 g, 63 mmol). After stirring for 5 h, cis-3-(4-fluorophenoxy)cyclopentanecarbaldehyde (4.00 g, 9.2 mmol) was added to the mixture and the whole stirred overnight at room temperature (*Tetrahedron Lett.*, 1972, 3769). The reaction mixture was filtered through a short columnmn of silica gel and the filtrate concentrated in vacuo to afford 6.12 g (85%) of title compound as a light yellow oil: $^1H$ NMR δ7.06–6.93 (m, 2H), 6.85–6.73 (m, 2H), 6.45 (d, J=9.2 Hz, 1H), 4.75–4.68 (m, 1H), 2.91–2.76 (m, 1H), 2.44–2.30 (m, 1H), 2.08–1.55 (m, 5H).

(v) 4-{cis-3-(4-Fluorophenoxy)cyclopentyl}-3-butyn-2-ol

A solution of 1,1 -dibromo-2-{cis-3-(4-fluorophenoxy) cyclopentyl}ethene (6.12 g, 18 mmol) in dry THF (50 ml) at −78° C. under an argon atmosphere was added n-butyllithium (24.5 ml, 39 mmol, 1.6M n-hexane solution). The mixture was stirred for 0.5 h at the same temperature and then allowed to warm to room temperature over 1 h. The mixture was cooled to 0° C., a solution of dry acetaldehyde (1.76 g, 40 mmol) in dry THF (20 ml) added to the mixture and the whole stirred overnight at room temperature. The reaction was quenched by the addition of saturated aqueous ammonium chloride solution (100 ml) and the whole extracted with ethyl acetate (200 ml). The combined extracts were washed with brine (200 ml), dried ($MgSO_4$) and concentrated in vacuo. Purification by column chromatography {$SiO_2$, 250 g; hexane/ethyl acetate (4:1)} afforded 2.18 g (49%) of title compound as a yellow oil: $^1H$ NMR δ7.05–6.92 (m, 2H), 6.86–6.77 (m, 2H), 4.78–4.62 (m, 1H), 4.60–4.48 (m, 1H), 2.81–2.65 (m, 1H), 2.52–2.36 (m, 1H), 2.12–1.81 (m, 5H), 1.65 (br.s, 1H), 1.45–1.40 (m, 3H).

(vi) N,o-Bis(tert-butoxycarbonyl)-N-[4-{cis- 3-(4-fluorophenoxy)cyclopentyl}-3-butyn-2-yl] hydroxylamine.

To a stirred solution of 4-{cis-3-(4-fluorophenoxy) cyclopentyl}-3-butyn-2-ol (2.18 g, 8.8 mmol), N,o-bis-(tert-butoxycarbonyl)hydroxylamine (2.30 g, 10 mmol) and triphenylphosphine (2.60 g, 10 mmol) in dry THF (50 ml) cooled to 0° C. was added dropwise diethyl azodicarboxylate (2.10 g, 12 mmol) in dry THF (10 ml) under an argon atmosphere. After completion of addition, the mixture was allowed to warm to room temperature, stirred for 1 h, and then volatiles removed under reduced pressure. Chromatographic purification of the residue {SiO$_2$, 250 g; hexane/ethyl acetate (15:1)} provided 3.70 g (91%) of the title compound as a pale yellow oil: $^1$H NMR δ7.01–6.90 (m, 2H), 6.85–6.72 (m, 2H), 5.10–4.89 (m, 1H), 4.70–4.62 (m, 1H), 2.78–2.63 (m, 1H), 2.51–2.33 (m, 1H), 2.01–1.46 (m, 23H), 1.41 (d, J=6.6 Hz, 3H).

(vii) N-[4-{cis-3-(4-Fluorophenoxy)cyclopentyl}-3-butyn-2-yl]-N-hydroxyurea

To a stirred solution of N,o-bis(tert-butoxycarbonyl)-N-[4-{cis-3-(4-fluorophenoxy)cyclopentyl }-3-butyn-2-yl] hydroxylamine (3.70 g, 8.0 mmol) in methylene chloride (50 ml) was added trifluoroacetic acid (15 ml) and the mixture stirred for 1 h at room temperature. Volatiles were removed under reduced pressure and ethyl acetate (100 ml ) added. The organic layer was washed with water (100 ml), saturated aqueous sodium hydrogen carbonate solution (100 ml ) and brine (100 ml). The organic phase was dried (MgSO$_4$) and concentrated under reduced pressure to afford crude deprotected hydroxylamine as white solids.

To a solution of the hydroxylamine (1.85 g, 7.5 mmol) in THF (20 ml) was added trimethylsilyl isocyanate (2.00 ml, 12 mmol) and the whole stirred for 30 min. Volatiles were removed under reduced pressure and the residue purified by silica gel column chromatography {SiO$_2$, 30 g; chloroform/acetone (2:1 )}. Recrystallization from diisopropyl ether/ethyl acetate gave 0.678 g (50%) of the title compound as a white powder: mp 95.6°–96.7° C.; IR (KBr) v 3460, 3350, 3100, 2880, 1640, 1595, 1540, 1510, 1480, 1460, 1210, 825 cm$^{-1}$; $^1$H NMR (DMSO-d$_6$) δ9.14 (s, 1H), 7.13–7.02 (m, 2H), 6.95–6.84 (m, 2H), 6.43 (s, 2H), 4.91–4.80 (m, 1H), 4.79–4.68 (m, 1H), 2.77–2.60 (m, 1H), 2.52–2.38 (m, 1H), 2.01–1.50 (m, 5H), 1.22 (d, J=7.0 Hz, 3H). Anal. Calcd for C$_{16}$H$_{19}$N$_2$O$_3$F: C, 62.73; H, 6.25; N, 9.14; F, 6.20. Found: C, 62.69; H, 6.40; N, 8.97; F, 6.11.

Example 2

Preparation of N-[4-{trans-3-(4-fluorophenoxy) cyclopentyl}-3-butyn-2-yl]-n-hydroxyurea trans-3-(4-Fluorophenoxy)cyclopentanecarbaldehyde was converted to the title compound as described for the preparation for N-[4-{cis-3(4-fluorophenoxy)cyclopentyl }-3-butyn-2-yl]-N-hydroxyurea in Example 1: mp 87.8°–88.5° C.; IR (KBr) v 3460, 3350, 3110, 2890, 1640, 1595, 1510, 1460, 1370, 1245, 1220, 1180, 1140, 830 cm$^{-1}$; $^1$H NMR (DMSO-d$_6$) δ9.13 (s, 1H), 7.15–7.03 (m, 2H), 6.94–6.83 (m, 2H), 6.45 (s, 2H), 4.91–4.76 (m, 2H), 2.90–2.78 (m, 1H), 2.22–1.95 (m, 3H), 1.92–1.78 (m, 1H), 1.75–1.48 (m, 2H), 1.22 (d, J=7.0 Hz, 3H). Anal. Calcd for C$_{16}$H$_{19}$N$_2$O$_3$F: C, 62.73; H, 6.25; N, 9.14; F, 6.20. Found: C, 62.44; H, 6.39; N, 8.95; F, 6.05.

Example 3

Preparation of N-[4-{cis-3-(4-fluorophenoxy) cyclobutyl}-3-butyn-2-yl]-N-hydroxyurea (i) Ethyl cis-3-benzyloxycyclobutanecarboxylate and ethyl trans-3-benzyloxycyclobutanecarboxylate A diastereomeric mixture of ethyl 3-benzyloxycyclobutanecarboxylate was obtained from epi-bromohydrin, benzyl bromide, and diethyl malonate according to the literature procedure (*J. Org. Chem.*, 1968, 33, 1959). Chromatographic separation on silica gel using hexane/ethyl acetate (5:1) as eluant afforded ethyl cis-3-benzyloxycyclobutanecarboxylate (Rf=0.4) and ethyl trans-3-benzyloxycyclobutanecarboxylate (Rf=0.5), respectively, as colorless oils: ethyl cis-3-benzyloxycyclobutanecarboxylate; $^1$H NMR δ7.37–7.24 (m, 5H), 4.43 (s, 2H), 4.13 (q, J=7.1 Hz, 2H), 4.03–3.89 (m, 1H), 2.68–2.41 (m, 3H), 2.30–2.18 (m, 2H), 1.25 (t, J=7.1 Hz, 3H): ethyl trans-3-benzyloxycyclobutanecarboxylate; $^1$H NMR δ7.37–7.26 (m, 5H), 4.42 (s, 2H), 4.33–4.22 (m, 1H), 4.14 (q, J=7.1 Hz, 2H), 3.07–2.97 (m, 1H), 2.56–2.44 (m, 2H), 2.38–2.20 (m, 2H), 1.26 (t, J=7.1 Hz, 3H).

(ii) Ethyl trans-3-hydroxycyclobutanecarboxylate

Ethyl trans-3-benzyloxycyclobutanecarboxylate was converted to the title compound as described in the literature procedure (*Tetrahedron*, 1965, 21, 2749): $^1$H NMR δ4.63–4.51 (m, 1H), 4.15 (q, J=7.1 Hz, 2H), 3.10–2.95 (m, 1H), 2.66–2.52 (m, 2H), 2.30–2.15 (m, 2H), 1.91 (br.s, 1H), 1.26 (t, J=7.1 Hz, 3H).

(iii) Ethyl cis-3-(4-fluorophenoxy) cyclobutanecarboxylate

Ethyl trans-3-hydroxycyclobutanecarboxylate was converted to the title compound as described for the preparation of 1-(1,3-dithian-2-yl)-3-(4-fluorophenoxy)cyclopentane: $^1$H NMR δ7.01–6.90 (m, 2H), 6.82–6.70 (m, 2H), 4.59–4.45 (m, 1H), 4.15 (q, J=7.1 Hz, 2H), 2.86–2.65 (m, 3H), 2.51–2.37 (m, 2H), 1.27 (t, J=7.1 Hz, 3H).

(iv) cis-3-(4-Fluorophenoxy) cyclobutanecarbaldehyde

To a solution of ethyl cis-3-(4-fluorophenoxy) cyclobutanecarboxylate (5.07 g, 21.3 mmol) in dry methylene chloride (100 ml) cooled to –78° C. was added dropwise diisobutylaluminum hydride (23.7 ml, 22.0 mmol, 0.93M in hexane) under an argon atmosphere. After completion of addition, the mixture was stirred at the same temperature for 0.5 h. Methanol (5 ml) was carefully added to the reaction mixture at –78° C. and the whole allowed to warm to room temperature over 1 h. 2N aqueous hydrochloric acid (200 ml) was added, the whole extracted with ethyl acetate (300 ml) and the combined extracts washed with brine (200 ml). The organic layer was dried (MgSO$_4$) and concentrated in vacuo. Chromatographic purification of the residue {SiO$_2$, 300 g; hexane/ethyl acetate (4:1)} provided 3.20 g (78%) of title compound as a colorless oil: $^1$H NMR δ9.73 (d, J=2.6 Hz, 1H), 7.03–6.91 (m, 2H), 6.80–6.70 (m, 2H), 4.72–4.59 (m, 1H), 2.97–2.83 (m, 1H), 2.75–2.61 (m, 2H), 2.48–2.33 (m, 2H).

(v) N-[4-{cis-3-(4-Fluorophenoxy)cyclobutyl}-3-butyn-2-yl]-N-hydroxyurea cis-3-(4-Fluorophenoxy)cyclobutanecarbaldehyde was converted to the title compound as described in the preparation for N-[4-{cis-3-(4-fluorophenoxy)cyclopentyl }-3-butyn-2-yl]-N-hydroxyurea in Example 1: mp 129.6°–130.3° C.; IR (KBr) v 3480, 3700, 3500, 3000, 2950, 2900, 1660, 1610, 1595, 1510, 1480, 1460, 1445, 1230, 1220, 825 cm$^{-1}$; $^1$H NMR (DMSO-d$_6$) δ9.17 (s, 1H), 7.20–7.03 (m, 2H), 6.91–6.79 (m, 2H), 6.45 (s, 2H), 4.95–4.82 (m, 1H), 4.60–4.46 (m, 1H), 2.90–2.62 (m, 3H), 2.09–1.95 (m, 2H), 1.22 (d, J=7.0 Hz, 3H). Anal. Calcd for C$_{15}$H$_{17}$N$_2$O$_3$F: C, 61.64; H, 5.86; N, 9.58; F, 6.50. Found: C, 61.60; H, 5.91: N, 9.49; F, 6.46.

Example 4

Preparation of N-[4-{trans-3-(4-fluorophenoxy) cyclobutyl}-3-butyn-2-yl]-N-hydroxyurea Ethyl cis-3-benzyloxycyclobutanecarboxylate was converted to the title compound as described for the preparation of N-[4-{cis-3-(4-fluorophenoxy)cyclobutyl}-3-butyn-2-yl]-N-hydroxyurea in Example 3: mp 115.7°–116.5° C.; IR (KBr) v 3495, 3470, 3440, 3000, 2950, 2900, 1660, 1570, 1510, 1480, 1450, 1430, 1250, 1220, 1100, 1085, 830, 760 cm$^{-1}$; $^1$H NMR (DMSO-d$_6$) δ9.12 (s, 1H), 7.15–7.02 (m, 2H), 6.87–6.76 (m, 2H), 6.48 (s, 2H), 4.98–4.79 (m, 2H), 3.23–3.05 (m, 1H), 2.50–2.23 (m, 4H), 1.25 (d, J=7.0 Hz, 3H). Anal. Calcd for $C_{15}H_{17}N_2O_3F$: C, 61.64; H, 5.86; N, 9.58; F, 6.50. Found: C, 61.61; H, 5.88; N, 9.38; F, 6.45.

Example 5

Preparation of N-hydroxy-N-(1S,3S)-3-phenoxycyclopentylurea (i) (1R,3S)-1-(tert-Butyldimethylsilyl)oxy-3-tetrahydropyranyloxycyclopentane A mixture of (1R,4S)-4-(tert-butyldimethylsilyl)oxy-2-cyclopentenol (9.70 g, 40 mmol) (*J. Amer. Chem. Soc.*, 1991, 113, 9851,), dihydropyran (4.40 g, 53.0 mmol) and p-toluenesulfonic acid (100 mg) in dry ether (50 ml) was stirred for 10 h at room temperature. The reaction mixture was washed with saturated aqueous sodium hydrogen carbonate solution (50 ml) and brine (50 ml). The organic phase was dried (MgSO$_4$) and concentrated under reduced pressure to afford 14.2 g of crude tetrahydropyranyl ether of (1R,4S)-4-(tert-butyldimethylsilyl)oxy-2-cyclopentenol as a colorless oil.

Catalytic hydrogenation (5% palladium on activated carbon) of the tetrahydropyranyl ether by standard procedure gave 11.3 g (83%) of title compound as a colorless oil: $^1$H NMR δ4.70–4.56 (m, 1H), 4.22–4.10 (m, 2H), 3.97–3.85 (m, 1H), 3.60–3.41 (m, 1H), 2.21–1.33 (m, 12H), 0.88 (s, 9H), 0.05–0.02 (m, 6H).

(ii) (1R,3S)-3-Tetrahydropyranyloxycyclopentanol

To a stirred solution of (1R,3S)-1-(tert-butyldimethylsilyl)oxy-3-tetrahydropyranyloxycyclopentane (11.3 g, 33.0 mmol) in dry THF (40 ml) was added a 1.0M solution of tetrabutylammonium fluoride in THF (50 ml, 50.0 mmol). After stirring for 1 h at room temperature, the reaction mixture was poured into water (200 ml) and the whole extracted with ether (200 ml). The ether phase was washed with brine (200 ml), dried (MgSO$_4$) and concentrated under reduced pressure. Chromatographic purification of the residue {SiO$_2$, 800 g; hexane/ethyl acetate (2:1) with 1% of triethylamine} provided 5.47 g (73%) of the title compound as a colorless oil: $^1$H NMR δ4.73–4.64 (m, 1H), 4.42–4.23 (m, 2H), 3.95–3.81 (m, 1H), 3.59–3.44 (m, 1H), 2.20–1.20 (m, 13H).

(iii) (1S,3S)-1-Phenoxy-3-tetrahydropyranyloxycyclopentane

To a stirred solution of (1R,3S)-3-tetrahydropyranyloxycyclopentanol (2.00 g, 10.7 mmol), phenol (1.20 g, 12.0 mmol) and triphenylphosphine (3.20 g, 12.0 mmol) in dry THF (40 ml) cooled to 0° C. was added dropwise a solution of diethyl azodicarboxylate (2.60 g, 15.0 mmol) in dry THF (10 ml). The mixture was stirred for 1 h at room temperature and then the volatiles removed under reduced pressure. Chromatographic purification of the residue {SiO$_2$, 150 g; hexane/ethyl acetate (20:1)} provided 2.16 g (77 %) of the title compound as a colorless oil: $^1$H NMR δ7.33–7.22 (m, 2H), 6.99–6.83 (m, 3H), 4.98–4.81 (m, 1H), 4.70–4.60 (m, 1H), 4.55–4.41 (m, 1H), 4.00–3.85 (m, 1H), 3.58–3.47 (m, 1H), 2.30–1.45 (m, 12H).

(iv) (1S,3S)-3-Phenoxycyclopentanol

To a stirred solution of (1S,3S)-1-phenoxy-3-tetrahydropyranyloxycyclopentane (2.16 g, 8.20 mmol) in methanol (50 ml) was added 6N aqueous hydrochloric acid (5 ml) and the mixture stirred for 2 h at room temperature. Volatiles were removed under reduced pressure and chromatographic purification of the residue {SiO$_2$, 150 g; hexane/ethyl acetate (3:1 )} provided 1.33 g (91%) of the title compound as a colorless oil: $^1$H NMR δ7.35–7.20 (m, 2H), 6.98–6.82 (m, 3H), 4.97–4.88 (m, 1H), 4.60–4.50 (m, 1H), 2.32–2.01 (m, 4H), 1.97–1.83 (m, 1H), 1.75–1.40 (m, 2H).

(v) (1R,3S)-3-Phenoxycyclopentanol

To a stirred solution of (1S,3S)-3-phenoxycyclopentanol (1.33 g, 7.50 mmol), benzoic acid (1.00 g, 8.50 mmol) and triphenylphosphine (2.20 g, 8.50 mmol) in dry THF (40 ml) cooled to 0° C. was added dropwise a solution of diethyl azodicarboxylate (1.74 g, 10.0 mmol) in dry THF (10 ml). The mixture was stirred for 1 h at room temperature and then the volatiles removed under reduced pressure. The residue was suspended in ether (20 ml) and insoluble material removed by filtration. The ether layer was concentrated in vacuo to afford 2.21 g of crude benzoate as a yellow oil.

Without purification, to a solution of the benzoate in methanol (30 ml) was added an aqueous solution of potassium hydroxide (5.00 g in 5 ml of water) and the whole stirred for 1 h. The volatiles were removed under reduced pressure, the residue diluted with water (50 ml) and the aqueous mixture extracted with diethyl ether (50 ml). The organic phase was washed with brine (50 ml), dried (MgSO$_4$) and concentrated in vacuo. The resultant oil was purified by flash column chromatography {SiO$_2$, 150 g; hexane/ethyl acetate (3:1)} to afford 1.27 g (95 %) of the title compound as a colorless oil: $^1$H NMR δ7.38–7.20 (m, 2H), 7.00–6.83 (m, 3H), 4.90–4.81 (m, 1H), 4.45–4.30 (m, 1H), 2.36–1.87 (m, 6H), 1.59 (br.s, 1H).

(vi) N-Hydroxy-N-(1S,3S)-3-phenoxycyclopentylurea (1 R,3S)-3-Phenoxycyclopentanol was converted to the title compound as described for the preparation of N-[4-{cis-3-(4-fluorophenoxy)cyclopentyl}-3-butyn-2-yl]-N-hydroxyurea in Example 1: mp 133.6°–134.0° C.; IR (KBr) v 3480, 3330, 2880, 1660, 1600, 1570, 1490, 1240, 1170 cm$^{-1}$; $^1$H NMR (DMSO-d$_6$) δ9.11 (s, 1H), 7.31–7.22 (m, 2H), 6.94–6.84 (m, 3H), 6.31 (s, 2H), 4.88–4.67 (m, 2H), 2.17–1.95 (m, 2H), 1.90–1.59 (m, 4H). Anal. Calcd for $C_{12}H_{16}N_2O_3$: C, 61.00; H, 6.83; N, 11.86. Found: C, 61.34; H, 7.04; N, 11.77.

Example 6

Preparation of N-hydroxy-N-(cis-3-phenylthiocyclopentyl)urea (i) 3-Phenylthiocyclopentanone oxime To a solution of 3-phenylthiocyclopentanone (*Syn. Commun.*, 1987, 17, 1607) (6.00 g, 30 mmol) in dry pyridine (50 ml) was added hydroxylamine hydrochloride (3.20 g, 45 mmol) and the reaction mixture was stirred for 3 h at room temperature. After the solvent was evaporated off, the residue was partitioned between water (50 ml) and ethyl acetate (100 ml), the aqueous layer separated and extracted with ethyl acetate (100 ml). The combined organic layer was washed with 1N aqueous hydrochloric acid (100 ml), saturated aqueous sodium hydrogen carbonate solution (100 ml) and brine (100 ml), dried (MgSO$_4$) and concentrated under reduced pressure to afford 6.10 g (98%) of the title compound as a pale yellow oil: $^1$H NMR δ7.42–7.38 (m, 2H), 7.33–7.22 (m, 3H), 3.71 (m, 1H), 3.00–3.24 (m, 4H), 2.16 (m, 1H), 1.86 (m, 1H).

(ii) N-Hydroxy-N-(cis-3-phenylthiocyclopentyl)urea

To a solution of 3-phenylthiocyclopentanone oxime (3.00 g, 14 mmol) in acetic acid (20 ml) was added sodium cyanoborohydride (1.80 g, 28 mmol) portionwise in solid form. After completion of addition, the whole was stirred for 1 h at room temperature, and then poured into saturated aqueous sodium hydrogen carbonate solution (100 ml). The reaction mixture was extracted with ethyl acetate (200 ml), the organic phase was washed with brine (200 ml), dried (MgSO$_4$) and concentrated under reduced pressure. The resultant residue was chromatographed on silica gel {SiO$_2$, 150 g; hexane/ethyl acetate (2:1)} to afford 1.80 g (62%) of hydroxylamine.

To a solution of the hydroxylamine obtained as above in dry THF (15 ml) was added trimethylsilyl isocyanate (1.50 ml, 11 mmol), and the reaction mixture stirred for 1 h at room temperature. Methanol (5 ml) was added and 10 min later solvent removed by evaporation. The residue was recrystallized from methanol/ethyl acetate/hexane to give 1.00 g (52%) of the title compound as white solids: mp 146.3°–147.5° C.; IR (KBr) v 3450, 3200, 1660, 1620, 1570, 1150, 1100 cm$^{-1}$; $^1$H NMR (DMSO-d$_6$) δ9.08 (s, 1H), 7.33 (m, 4H), 7.19 (m, 1H), 6.28 (br s, 2H), 4.56 (m, 1H), 3.58 (m, 1H), 2.15–1.56 (m, 6H). Anal. Calcd for C$_{12}$H$_{16}$N$_2$O$_2$S: C, 57.12; H, 6.39; N, 11.10; S, 12.71. Found: C, 57.03; H, 6.50: N, 11.02; S, 12.78.

Example 7

Preparation of N-hydroxy-N-trans-3-phenylthiocyclopentyl urea

The mother liquor obtained from Example 6 was concentrated under reduced pressure and the residue recrystallized from methanol/ethyl acetate to give 310 mg (17%) of the title compound as white solids: mp 116.1°–118.0° C.; IR (KBr) v 3400, 3200, 1660, 1580, 1440, 840 cm$^{-1}$; $^1$H NMR (DMSO-d$_6$) δ59.11 (s, 1H), 7.32 (m, 411), 7.24 (m, 1H), 6.29 (br s, 2H), 4.70 (m, 1H), 3.77 (m, 1H), 2.13 (m, 2H), 1.85 (m, 1H), 1.77–1.59 (m, 2H), 1.47 (m, 1H). Anal. Calcd for C$_{12}$H$_{16}$N$_2$O$_2$S: C, 57.12; H, 6.39; N, 11.10; S, 12.71. Found: C, 57.06; H, 6.43; N, 11.01; S, 12.91.

Example 8

Preparation of N-[1-{3-(4-fluorophenoxy) cyclopentyl}ethyl]-N-hydroxyurea (i) 1-{3-(4-1Fluorophenoxy)cyclopentyl}ethanol To a solution of 3-(4-fluorophenoxy) cyclopentanecarbaldehyde (2.35 g, 11.3 mmol) in dry THF (30 ml) cooled to –78° C. was added dropwise a solution of methylmagnesium bromide (16.9 ml, 16.2 mmol, 0.96N in THF) under an argon atmosphere. After completion of addition, the mixture was allowed to warm to room temperature over 4 h and then the reaction was quenched by the addition of saturated aqueous ammonium chloride solution (50 ml) and the whole extracted with ethyl acetate (100 ml). The combined extracts were washed with brine (100 ml), dried (MgSO$_4$) and concentrated in vacuo. Purification by column chromatography {SiO$_2$, 250 g; hexane/ethyl acetate (4:1)} afforded 1.65 g (65%) of the title compound as a colorless oil: $^1$NMR δ7.00–6.91 (m, 2H), 6.86–6.78 (m, 2H), 4.79–4.68 (m, 1H), 3.80–3.58 (m, 1H), 2.30–1.78 (m, 5H), 1.70–1.35 (m, 3H), 1.25–1.17 (m, 3H).

(ii) N-[1-{3-(4-Fluorophenoxy)cyclopentyl}ethyl]-N-hydroxyurea

1-{3-(4-Fluorophenoxy)cyclopentyl}ethanol was converted to the title compound as described for the preparation of N-[4-{cis-3-(4-fluorophenoxy)cyclopentyl }-3-butyn-2-yl]-N-hydroxyurea in Example 1: mp 111.0°–112.5° C.; IR (KBr) v 3460, 3340, 3200, 1665, 1575, 1510, 1450, 1210, 825 cm$^{-1}$; $^1$H NMR (DMSO-d$_6$) δ9.21 (s), 9.19 (s), 8.88 (s, 1H), 7.15–7.03 (m, 2H), 6.96–6.85 (m, 2H), 6.20 (s, 2H), 4.83–4.68 (m, 1H), 3.99–3.80 (m, 1H), 2.35–1.18 (m, 7H), 1.04–0.95 (m, 3H). Anal. Calcd for C$_{14}$H$_{19}$N$_2$O$_3$F: C, 59.56; H, 6.78; N, 9.92, F, 6.73. Found: C, 59.32; H, 6.90; N, 10.12, F, 6.79.

Example 9

Preparation of (+)-N-[4- {cis-3-4-fluorophenoxy) cyclobutyl}-3-butyn-2yl]-N-hydroxyurea Racemic N-[4-{cis-3-(4-fluorophenoxy)cyclobutyl}-3-butyn-2-yl]-N-hydroxyurea (Example 3) was separated using a chiral HPLC column (Daicel CHIRALPAK AS 0.46×25 cm; mobile phase: ethanol/n-hexane (20:80); flow rate, 1 ml/min; temperature: room temperature; detector: λ=230 nm) to afford title compound (retention time: 11.3 min) and the enantiomer (Example 10, retention time: 17.6 min). Respective enantiomers were further purified by chromatography (SiO$_2$, ethyl acetate) and recrystallized from diisopropyl ether/ethyl acetate. Optical purities were ≧99.5%. Title compound (white solids): mp 122°–124° C.; [α]$_D$+48.5° (c 0.0258, ethanol); Anal. Calcd for C$_{15}$H$_{17}$N$_2$O$_3$F: C, 61.64; H, 5.86; N, 9.58. Found: C, 61.44; H, 5.81; N, 9.53.

Example 10

Preparation of (–)-N-[4-{cis-3-4-fluorophenoxy) cyclobutyl}-3-butyn-2-yl]-N-hydroxyurea The title compound (white solids): mp 123°–125° C.; [α]$_D$–39.5° (c 0.0294, ethanol); Anal. Calcd for C$_{15}$H$_{17}$N$_2$O$_3$F: C, 61.64; H, 5.86; N, 9.58. Found: C, 1.45; H, 5.90; N, 9.49.

Example 11

Preparation of (+)-N-[4-{trans-3-(4-fluorophenoxy) cyclobutyl}-3 -butyn-2-yl]-N-hydroxyurea and (–)-N-[4{trans-3 -(4-fluorophenoxy)cyclobutyl}-3-butyn-2-yl]-N-hydroxyurea The title compounds were separeted by a manner similar to that of Example 9 and Example 10 from the corresponding racemic N-[4-{trans-3-(4-fluorophenoxy)cyclobutyl }-3-butyn-2-yl]-N-hydroxyurea in Example 4. The retention time was 10.5 min. and 15.2 min.

(+)-N-[4-{trans-3-(4-fluorophenoxy)cyclobutyl}-3-butyn-2-yl]-N-hydroxyurea: mp 125°–127° C.; [α]$_D$+34.60 (c 0.0260, ethanol); Anal. Calcd for C$_{15}$H$_{17}$N$_2$O$_3$F: C, 61.64; H, 5.86; N, 9.58. Found: C, 61.53; H, 5.99; N, 9.63.

(–)-N-[4-{trans-3-(4-fluorophenoxy)cyclobutyl}-3-butyn-2-yl]-N-hydroxyurea: mp 124°–126°; [α]$_D$–23.7° (c 0.0282, ethanol); Anal. Calcd for $C_{15}H_{17}N_2O_3F$: C, 61.64; H, 5.86; N, 9.58. Found: C, 61.80; H, 6.03; N, 9.60.

Example 12

Preparation of (+)-N-[4-{cis-3-(4-chlorophenoxy) cyclobutyl}-3-butyn-2-yl]-N-hydroxyurea and (−)-N-[4-{cis-3-94-chlorophenoxy)cyclobutyl}-3-butyn-2yl]-N-hydroxyurea

(i) Ethyl cis-3-hydroxycyclobutanecarboxylate

To a cooled (−30° C.) solution of ethyl 3-oxocyclobutanecarboxylate (J. Org. Chem. 1988, 53, 3481) (18.1 g, 130 mmol) in ethanol (100 ml) was added $NaBH_4$ (4.92 g, 130 mmol) in small potions over 0.25 h. The reaction mixture was stirred at −30° C. for 0.5 h and then at room temperature for 0.5 h. The reaction mixture was poured into water (200 ml) and extracted with ether (500 ml). The organic phase was washed with brine (200 ml), dried ($MgSO_4$) and concentrated. The residue was distilled to afford 15.1 g (81%) of ethyl cis-3-hydroxycyclobutanecarboxylate as a colorless oil: bp 86°–88° C. (1 mmHg); $^1$H NMR δ4.24 (m, 3H), 2.66–2.52 (m, 3H), 2.28–2.09 (m, 2H), 2.03 (br s, 1H), 1.26 (t, J=7.3 Hz, 3H).

(ii) Ethyl trans-3-(4-methoxyphenoxy) cyclobutanecarboxylate

To a stirred solution of ethyl cis-3-hydroxycyclobutanecarboxylate (1.32 g, 9.20 mmol), 4-methoxyphenol (3.43 g, 27.6 mmol) and triphenylphosphine (3.12 g, 11.9 mmol) in dry THF (25 ml) was added dropwise diethyl azodicarboxylate (2.07 g, 11.9 mmol) in dry THF (5 ml) under argon atmosphere at room temperature. After completion of addition, the mixture was heated to 80° C., maintained at the same temperature for 1 h, and then volatiles removed under reduced pressure. Chromatographic purification of the residue {$SiO_2$, 150 g; hexane/ethyl acetate (20/1)} provided 1.96 g (85%) of ethyl trans-3-(4-methoxyphenoxy)cyclobutanecarboxylate as a colorless oil. $^1$H NMR δ56.85–6.69 (m, 4H), 4.90–4.80 (m, 1H), 4.18 (q, J=7.0 Hz, 2H), 3.76 (s, 3H), 3.20–3.09 (m, 1H), 2.78–2.62 (m, 2H), 2.5–2.35 (m, 2H), 1.29 (t, J=7.0 Hz, 3H).

(iii) {trans-3-(4-Methoxyphenoxy) cyclobutyl}methanol

To a stirred suspension of lithium aluminum hydride (389 mg, 10.0 mmol) in ether (413 ml) was added a solution of ethyl trans-3-(4-methoxyphenoxy)cyclobutanecarboxylate (1.97 g, 7.9 mmol) in ether (10 ml) at 0° C. and the mixture stirred for 1 h at room temperature. Water (3 ml) was carefully added to the reaction mixture at 0° C. and the whole allowed to warm to room temperature. 1 N aqueous hydrochloric acid (50 ml) was added, the ether phase separated and the aqueous phase extracted with ethyl acetate (100 ml). The combined organic phase was dried ($MgSO_4$) and concentrated in vacuo to provide 1.99 g (quant.) of {trans-3-(4-methoxyphenoxy)-cyclobutyl}methanol as white solids. The product was used without further purification: $^1$H NMR δ6.88–6.70 (m, 4H), 4.75–4.62 (m, 1H), 3.76 (s, 3H), 3.71 (d, J=6.6 Hz, 2H), 2.62–2.46 (m, 1H), 2.35–2.28 (m, 4H), 1.59 (s, 1H).

(iv) trans-3-( 4-Methoxyphenoxy )cyclobutanecarbaldehyde

To a stirred mixture of {trans-3-(4-methoxyphenoxy) cyclobutyl}methanol (19.8 g, 95.3 mmol), N-methylmorpholine N-oxide (16.7 g, 143 mmol) and powdered 4A molecular sieves (48 g) in methylene chloride (190 ml) was added solid tetrapropylammonium perruthenate (1.67 g, 4.80 mmol) at room temperature under argon atmosphere. On completion, the mixture was filtered through a pad of silica, eluting with methylene chloride (500 ml). The filtrate was evaporated and the residue purified by silica-gel column chromatography {$SiO_2$, 500 g; hexane/ethyl acetate (3/1)} to afford 12.2 g (62%) of trans-3-(4-methoxyphenoxy)cyclobutanecarbaldehyde as white solids: $^1$H NMR δ9.88 (s, 1H), 6.88–6.65 (m, 4H), 4.75–4.58 (m, 1H), 3.76 (s, 3H), 3.31–3.15 (m, 1H), 2.82–2.61 (m, 2H), 2.54–2.25 (m, 3H).

(v) {trans-3-(4-Methoxyphenoxy)cyclobutyl}ethyne

A slurry of potassium tert-butoxide (7.85 g, 70 mmol) in THF (50 ml) was cooled to −78° C. under argon atmosphere. To this was added a solution of methyl (diazomethyl) phosphonate (J. Org. Chem. 1979, 44, 4997) (12.5 g, 70 mmol) in THF (100 ml), followed after 0.5 h by a solution of trans-3-(4-methoxyphenoxy)cyclobutanecarbaldehyde (12.1 g, 58.7 mmol) in THF (100 ml) at the same temperature. The resulting solution was stirred at −78° C. for 3 h and then maintained at room temperature for another 8 h. The reaction was quenched with water (300 ml) and the aqueous mixture was extracted with ethyl acetate. The combined organic extracts were washed with brine (200 ml), dried ($MgSO_4$) and concentrated in vacuo to give yellow solids. Silica-gel column chromatography of the solids {$SiO_2$, 800 g; hexane/ethyl acetate (9/1)} of the solids afforded 6.49 g (55%) of {trans-3-(4-methoxyphenoxy)cyclobutyl}ethyne as white solids: $^1$H NMR δ6.84–6.70 (m, 4H), 4.92–4.82 (m, 1H), 3.76 (s, 3H), 3.20–3.03 (m, 1H), 2.64–2.40 (m, 4H), 2.19 (s, 1H).

(vi) 4-{trans-3-(4-Methoxyphenoxy)cyclobutyl}-3-butyn-2-ol

A solution of {trans-3-(4-methoxyphenoxy)cyclobutyl }ethyne (6.40 g, 32.0 mmol) in THF (80 ml) at −78° C. under argon atmosphere was added n-butyllithium (23.7 ml, 38.0 mmol). The mixture was stirred for 0.5 h at the same temperature and then allowed to warm to −40° C. over 1 h. The mixture was recooled to −78° C., a solution of dry acetaldehyde (3.52 g, 80.0 mmol) in THF (20 ml) added to the mixture and the whole stirred overnight at room temperature. The reaction was quenched with saturated aqueous ammonium chloride solution (100 ml) and the whole extracted with ethyl acetate (200 ml). The combined extracts were washed with brine (200 ml), dried ($MgSO_4$) and concentrated in vacuo. Purification by column chromatography {$SiO_2$, 500 g; hexane/ethyl acetate (3/1)} afforded 7.58 g (97%) of 4-{trans-3-(4-methoxyphenoxy)cyclobutyl }-3-butyn-2-ol as white solids: $^1$H NMR δ6.85–6.68 (m, 4H), 4.89–4.78 (m, 1H), 4.62–4.50 (m, 1H), 3.76 (s, 3H), 3.22–3.09 (m, 1H), 2.59–2.40 (m, 4H), 1.65 (s, 1H), 1.45 (d, J=6.9 Hz, 3H).

(vii) N,o-bis(tert-Butoxycarbonyl)-N-[4-{trans- 3-(4-methoxyphenoxy)-cyclobutyl}-3-butyn-2-yl] hydroxylamine To a stirred solution of 4-{trans-3-(4-methoxyphenoxy) cyclobutyl}-3-butyn-2ol (7.55 g, 30.6 mmol), N,o-bis-(tert-butoxycarbonyl)hydroxylamine (9.33 g, 40.0 mmol) and triphenylphosphine (10.5 g, 40.0 mmol) in dry THF (80 ml) was added dropwise diethyl azodicarboxylate (7.84 g, 45.0 mmol) in dry THF (20 ml) at 0° C. under argon atmosphere.

After completion of addition, the mixture was allowed to warm to room temperature, stirred for 1 h at room temperature and then the volatiles were removed under reduced pressure. Chromatographic purification of the residue {SiO$_2$, 500 g; hexane/ethyl acetate (20/1)} provided 15.1 g (quant.) of N,o-bis(tert-butoxycarbonyl)-N-[4-{trans-3-(4-methoxyphenoxy)cyclobutyl}3-butyn-2-yl]hydroxylamine as a light red oil: $^1$H NMR δ6.85–6.68 (m, 4H), 5.12–4.90 (m, 1H), 4.87–4.76 (m, 1H), 3.76 (s, 3H), 3.18–3.02 (m, 1H), 2.57–2.35 (m, 4H), 1.60–1.40 (m, 18 H), 1.43 (d, J=7.0 Hz, 3H).

(viii) N,o-bis(tert-Butoxycarbonyl)-N-{4-(trans-3-hydroxycyclobutyl)-3-butyn-2-yl}hydroxylamine To a solution of N,o-bis(tert-butoxycarbonyl)-N-[4-{trans-3-(4-methoxyphenoxy)cyclobutyl }-3-butyn-2-yl] hydroxylamine in 4:1 mixture of acetonitrile and water (250 ml) was added ceric ammonium nitrate (74.0 g, 135 mmol) at 0° C. in small potions. The reaction mixture was stirred for 1 h at the same temperature, diluted with water (200 ml) and then extracted with ether (300 ml). The ether phase was washed with brine (200 ml), dried (MgSO$_4$) and concentrated in vacuo. Purification by flash column chromatography {SiO$_2$, 800 g; hexane/ethyl acetate (2/1)} gave 8.20 g (75%) of N,o-bis(tert-butoxycarbonyl )-N-{4-(trans-3-hydroxycyclobutyl)-3-butyn-2-yl}hydroxylamine as a yellow oil: $^1$H NMR (δ5.08–4.87 (m, 1H), 4.65–4.48 (m, 1H), 3.04–2.88 (m, 1H), 2.45–2.29 (m, 2H), 2.25–2.10 (m, 2 H), 1.77 (s, 1H), 1.70–1.10 (m, 18 H), 1.41 (d, J=7.0 Hz, 3H).

(ix) N,o-bis(tert-Butoxycarbonyl)-N-[4-{cis-3-(4-chlorophenoxy)cyclobutyl }-3-butyn-2-yl] hydroxylamine To a stirred solution of N,o-bis(tert-butoxycarbonyl)-N-{4-(trans-3-hydroxycyclobutyl)-3-butyn-2-yl }hydroxylamine (480 mg, 1.35 mmol), 4-chlorophenol (527 mg, 4.10 mmol) and triphenylphosphine (472 mg, 1.80 mmol) in dry THF (8 ml) was added dropwise diethyl azodicarboxylate (314 mg, 1.80 mmol) in dry THF (2 ml) under argon atmosphere at room temperature. After completion of addition, the mixture was heated to 80° C., maintained at the same temperature for 1 h, and then volatiles removed under reduced pressure. Chromatographic purification of the residue {SiO$_2$, 150 g; hexane/ethyl acetate (9/1)} provided 440 mg (70%) of N,o-bis( tert-butoxycarbonyl-N-[4-{cis-3-(4-chlorophenoxy)cyclobutyl}-3-butyn-2-yl]-hydroxylamine as a colorless oil: $^1$H NMR δ7.26–7.10 (m, 2H), 6.75–6.62 (m, 2H), 5.08–4.90 (m, 1H), 4.50–4.39 (m, 1H), 2.85–2.60 (m, 3H), 2.32–2.19 (m, 2H), 1.55–1.46 (m, 18 H), 1.41 (d, J=7.0 Hz, 3H).

(x) N-[4-{cis-3-(4-Chlorophenoxy)cyclobutyl}-3-butyn-2-yl]-N-hydroxyurea

To a stirred solution of N,o-bis(tert-butoxycarbonyl)-N-[4-{cis-3-(4-chlorophenoxy)cyclobutyl }-3-butyn-2-yl] hydroxylamine (440 mg, 0.94 mmol) in methylene chloride (10 ml) was added trifluoroacetic acid (4 ml) and the mixture stirred for 1 h at room temperature. Volatiles were removed under reduced pressure and ethyl acetate (50 ml) added. The organic layer was washed with water (50 ml), saturated aqueous sodium hydrogen carbonate solution (50 ml) and brine (50 ml). The organic phase was dried (MgSO$_4$) and concentrated under reduced pressure to afford 285 mg of crude deprotected hydroxylamine as white solids.

To a solution of the hydroxylamine in THF (10 ml) was added trimethylsilyl isocyanate (0.30 ml, 2.20 mmol) and the whole stirred for 0.5 h. Volatiles were removed under reduced pressure and the residue purified by silica gel column chromatography {SiO$_2$, 50 g; chloroform/acetone (2:1)} to give 268 mg (92 %) of racemic N-[4-{cis-3-(4-chlorophenoxy)cyclobutyl}-3-butyn-2-yl]-N-hydroxyurea as white solids: $^1$H NMR δ7.61 (br s, 1H), 7.22 (d, J=8.4 Hz, 2H), 6.70 (d, J=8.4 Hz, 2H), 5.62 (br s, 2H), 5.18–5.00 (m, 1H), 4.52–4.37 (m, 1H), 2.88–2.61 (m, 3H), 2.32–2.11 (m, 2H), 1.38 (d, J=6.6 Hz, 3H).

(xi) (+)-N-[4-{cis-3-(4-Chlorophenoxy)cyclobutyl}-3-butyn-2-yl]-N-hydroxyurea

Racemic N-[4-{cis-3 -(4-chlorophenoxy)cyclobutyl }-3-butyn -2 -yl]-N-hydroxyurea was separated using HPLC technique (column: DAICEL CHEMICAL INDUSTRIES, LTD; CHIRALPAK AS 2 cm×25 cm, eluent: hexane/ethanol (8/2), flow late: 5 ml/min., temperature: rt.). The 1st fraction was collected and evaporated to give the residue. This was purified by silica-gel column chromatography {SiO$_2$, 50 g; chloroform/acetone (2:1)}, followed by recrystalization from ethyl acetate to afford 67 mg of (+)-N-[4-{cis-3-(4-chlorophenoxy)cyclobutyl}-3-butyn-2-yl]-N- hydroxyurea as a white powder: [α]$_D$+28.6° (c 0.042, EtOH); mp 110.0°–109.2° C.; IR (KBr) v 3500, 3400, 3200, 3000, 2950, 2850, 1675, 1600, 1580, 1490, 1445, 1430, 1340, 1290, 1250, 1170, 1135, 1100, 1080, 825, 665 cm$^{-1}$; $^1$H NMR δ7.53 (br s, 1H), 7.21 (d, J=8.4 Hz, 2H), 6.69 (d, J=8.4 Hz, H), 5.60 (br s, 2H), 5.18–5.03 (m, 1H), 4.50–4.37 (m, 1H), 2.88–2.60 (m, 3H), 2.31–2.12 (m, 2H), 1.39 (d, J=6.6 Hz, 3H). Anal. Calcd for C$_{15}$H$_{17}$N$_2$O$_3$Cl: C, 58.35; H, 5.55; N, 9.07. Found: C, 58.04; H, 5.65; N, 8.68.

(xii) (−)-N-[4-{cis-3-(4-Chlorophenoxy)cyclobutyl}-3-butyn-2-yl]-N-hydroxyurea

The (−)-enantiomer was obtained from the 2nd fraction in the similar manner described above. 70 mg of (−)-N-[4-{cis-3-(4-chlorophenoxy)cyclobutyl}-3-butyn-2-yl]-N-hydroxyurea was afforded as a white powder: [α]$_D$−29.2° (c 0.048, EtOH); mp 110.0°–109.1° C; IR (KBr) v 3500, 3400, 3200, 3000, 2950, 2850, 1670, 1600, 1580, 1490, 1440, 1430, 1250, 1170, 1140, 1100, 1080, 820, 665 cm$^{-1}$; $^1$H NMR δ7.69 (br s, 1H), 7.20 (d, J=8.4 Hz, 2H), 6.69 (d, J=8.4 Hz, 2H), 5.64 (br s, 2H), 5.15–5.01 (m, 1H), 4.50–4.35 (m, 1H), 2.87–2.60 (m, 3H), 2.33–2.16 (m, 2H), 1.38 (d, J=6.6 Hz, 3H). Anal. Calcd for C$_{15}$H$_{17}$N$_2$O$_3$Cl: C, 58.35; H, 5.55; N, 9.07. Found: C, 58.45; H, 5.65; N, 8.79.

Example 13

(+)-N-Hydroxy-N-[4-{cis-3-(4-trifluoromethylphenoxy)cyclobutyl}-3-butyn-2-yl] urea The title compound was prepared in a manner similar to that of Example 12. [α]$_D$+38.1° (c 0.042, EtOH); mp 112.7°–113.6° C.; IR (KBr) v 3500, 3400, 3200, 3000, 2950, 2850, 1675, 1620, 1580, 1520, 1450, 1330, 1260, 1180, 1160, 1110 1070, 840 cm$^{-1}$; $^1$H NMR δ7.52 (d, J=8.4 Hz, 2H), 6.83 (d, J=8.4 Hz, 2H), 6.47 (s, 1H), 5.44 (s, 2H), 5.20–5.10 (m, 1H), 4.60–4.48 (m, 1H), 2.90–2.65 (m, 3H), 2.35–2.21 (m, 2H), 1.40 (d, J=7.0 Hz, 3H). Anal. Calcd for C$_{16}$H$_{17}$N$_2$O$_3$F: C, 56.14; H, 5.01; N, 8.18. Found: C, 56.32; H, 5.22; N, 7.77.

Example 14

(−)-N-Hydroxy-N-[4-{cis-3-(4-trifluoromethylphenoxy)cyclobutyl}-3-butyn-2-yl] urea The title compound was prepared in a manner similar to that of Example 12. [α]$_D$−33.3° (c 0.042, EtOH); mp 112.0°–112.8° C.; IR (KBr) ν 3500, 3400, 3200, 3000, 2950, 2850, 1680, 1620, 1580, 1520, 1450, 1430, 1340, 1260, 1180, 1160, 1110, 1070, 840, 770 cm$^{-1}$; $^1$H NMR δ7.52 (d, J=8.8 Hz, 2H), 6.84 (d, J=8.8 Hz, 2H), 6.02 (s, 1H), 5.37 (s, 2H), 5.20–5.09 (m, 1H), 4.61–4.48 (m, 1H), 2.90–2.64 (m, 3H), 2.37–2.20 (m, 2H), 1.41 (d, J=7.0 Hz, 3H). Anal. Calcd for $C_{16}H_{17}N_2O_3F$: C, 56.14; H, 5.01; N, 8.18. Found: C, 56.40; H, 5.30; N, 7.88.

Example 15

(+)-N-[4-{cis-3-(2-Chloro-4-fluorophenoxy) cyclobutyl}-3-butyn-2-yl]-N-hydroxyurea The title compound was prepared in a manner similar to that of Example 12. $[\alpha]_D$+33.3° (c 0.042, EtOH); mp 161.4°–161.9° C.; IR (KBr) ν 3500, 3350, 3200, 3000, 2950, 2900, 1640, 1590, 1490, 1440, 1340, 1450, 1290, 1270, 1200, 1140, 1080, 1160, 1150, 980, 860, 800 cm$^{-1}$; $^1$H NMR (DMSO-d$_6$) δ9.19 (s, 1H), 7.44 (dd, J=8.1, 2.9 Hz, 1H), 7.15 (ddd, J=9.2, 8.1, 2.9 Hz, 1H), 6.98 (dd, J=9.2, 5.1 Hz, 1H), 6.47 (s, 2H), 4.95–4.85 (m, 1H), 4.70–4.58 (m, 1H), 2.89–2.65 (m, 3H), 2.12–2.00 (m, 2H), 1.23 (d, J=7.0 Hz, 3H). Anal. Calcd for $C_{15}H_{16}N_2O_3ClF$: C, 55.14; H, 4.94; N, 8.57. Found: C, 55.07; H, 4.94; N, 8.55.

Example 16

(−)-N-[4{cis-3(2-Chloro-4-fluorophenoxy) cyclobutyl}3-butyn-2-yl]-N-hydroxyurea

The title compound was prepared in a manner similar to that of Example 12. $[\alpha]_D$–38.1°(C 0.042, EtOH); mp 159.5°–160.1° C.; IR (KBr) ν 3500, 3350, 3200, 3000, 2950, 2900, 1650, 1640, 1590, 1510, 1490, 1440, 1340, 1200, 1140, 1080, 1060, 1050, 980, 860, 800 cm$^{-1}$; $^1$H NMR (DMSO-d$_6$) δ9.19 (s, 1H), 7.43 (dd, J=8.4, 2.9 Hz, 1H), 7.14 (ddd, J=9.2, 8.4, 2.9 Hz, 1H), 6.98 (dd, J=9.2, 5.1 Hz, 1H), 6.47 (s, 2H), 4.94–4.83 (m, 1H), 4.69–4.55 (m, 1H), 2.90–2.60 (m, 3 H), 2.12–1.95 (m, 2H), 1.23 (d, J=6.6 Hz, 3H). Anal. Calcd for $C_{15}H_{16}N_2O_3ClF$, 55.14; H, 4.94; N, 8.57. Found: C, 55.21; H, 4.90; N, 8.63.

Example 17

(+)-N-[4-{cis-3-(4-Fluoro-2-methylphenoxy) cyclobutyl}-3-butyn-2-yl]-N-hydroxyurea The title compound was prepared in a manner similar to that of Example 12. $[\alpha]_H$+19.3° (c 0.044, EtOH); mp 143.7°–144.7° C.; IR (KBr) ν 3480, 3350, 3200, 3000, 2950, 1660, 1640, 1590, 1510, 1480, 1450, 1330, 1220, 1080, 980, 870, 800 cm$^{-1}$; $^1$H NMR (DMSO-d$_6$) δ9.18 (s, 1H), 7.02 (dd, J=9.2, 3.0 Hz, 1H), 6.90 (ddd, J=9.2, 8.8, 3.0 Hz, 1H), 6.72 (dd, J=8.8, 4.8 Hz, 1H), 6.47 (s, 2H), 4.93–4.84 (m, 1H), 4.59–4.45 (m, 1H), 2.88–2.60 (m, 3H), 2.15 (s, 3H), 2.10–1.93 (m, 2H), 1.23 (d, J=7.0 Hz, 3H). Anal. Calcd for $C_{16}H_{19}N_2O_3F$: C, 62.73; H, 6.25; N, 9.14. Found: C, 62.33; H, 6.25; N, 9.17.

Example 18

(−)-N-[4-{cis-3-(4-Fluoro-2-methylphenoxy) cyclobutyl}-3-butyn-2-yl]-N-hydroxyurea The title compound was prepared in a .manner similar to that of Example 12. $[\alpha]_D$–20.5° (C 0.044, EtOH); mp 139.2°–140.4° C.; IR (KBr) ν 3480, 3340, 3200, 3000, 2980, 2950, 2900, 1680, 1660, 1590, 1510, 1480, 1450, 1370, 1330, 1260, 1220, 1180, 1140, 1110, 1080, 980, 870, 800, 720 cm$^{-1}$; $^1$H NMR (DMSO-d$_6$) δ9.18 (s, 1H), 7.01 (dd, J=9.2, 2.9 Hz, 1H), 6.91 (ddd, J=9.2, 8.8, 2.9 Hz, 1 H), 6.72 (dd, J=8.8, 4.8 Hz, 1H), 6.47 (s, 2H), 4.95–4.84 (m, 1H), 4.58–4.45 (m, 1H), 2.88–2.63 (m, 3H), 2.14 (s, 3H), 2.10–1.92 (m, 2H), 1.23 (d, J=7.0 Hz, 3H). Anal. Calcd for $C_{16}H_{19}N_2O_3F$: C, 62.73; H, 6.25; N, 9.14. Found: C, 62.33; H, 6.25; N, 9.17.

Example 19

(+)-N-Hydroxy-N-[4-{cis-3-(4-trifluoromethyloxyphenoxy)cyclobutyl}-3-butyn-2-yl]urea The title compound was prepared in a manner similar to that of Example 12. $[\alpha]_D$+29.6° (c 0.025, EtOH); mp 103.0°–105.0° C.; IR (KBr) ν 3495, 3385, 1673, 1666, 1579, 1510, 1446, 1249 cm$^{-1}$; $^1$H NMR δ7.14–7.08 (m, 2H), 6.80–6.73 (m, 2H), 5.59 (s, 1H), 5.30 (br s, 2H), 5.16 (dq, J=1.5, 7.0 Hz, 1H), 4.54–4.42 (m, 1H), 2.88–2.64 (m, 3H), 2.37–2.22 (m, 2H), 1.41 (d, J=7.0 Hz, 3H). Anal. Calcd for $C_{16}H_{17}N_2O_4F_3$: C, 53.63; H, 4.78; N, 7.82. Found: C, 53.84; H, 4.84; N, 7.80.

Example 20

(−)-N-Hydroxy-N-[4-{cis-3-(4-trifluoromethyloxyphenoxy)cyclobutyl}-3-butyn-2-yl]urea The title compound was prepared in a manner similar to that of Example 12. $[\alpha]_D$–29.8° (C 0.071, EtOH); mp 103.0°–105.0° C.; IR (KBr) ν 3495, 3385, 1673, 1666, 1578, 1510, 1446, 1249 cm$^{-1}$; $^1$H NMR δ7.14–7.08 (m, 2H), 6.80–6.73 (m, 2H), 5.59 (s, 1H), 5.30 (br s, 2H), 5.16 (dq, J=1.5, 7.0 Hz, 1H), 4.54–4.42 (m, 1H), 2.88–2.64 (m, 3H), 2.37–2.22 (m, 2H), 1.41 (d, J=7.0 Hz, 3H). Anal. Calcd for $C_{16}H_{17}N_2O_4F_3$: C, 53.63; H, 4.78; N, 7.82. Found: C, 53.64; H. 4.77; N, 7.81.

We claim:

1. A compound of the chemical formula (I):

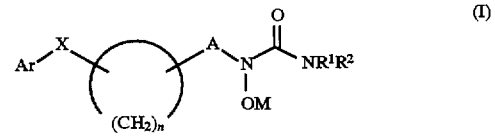

wherein $R^1$ and $R^2$ are each independently hydrogen or $C_1$–$C_4$alkyl;

Ar is phenyl or mono-, di- or trisubstituted phenyl;

A is a valence bond or a $C_1$–$C_6$ alkylene chain, optionally having one double bond or one triple bond in the chain, and optionally having one or more $C_1$–$C_4$ alkyl groups attached to the chain;

X is oxygen or sulfur;

n is an integer of 3 to 6;

M is hydrogen, pharmaceutically acceptable cation or a metabolically cleavable group; and X and A may be attached at any available position on the ring.

2. A compound according to claim 1 wherein Ar is phenyl or mono- or disubstituted phenyl, wherein each substituent is independently selected from halogen, $C_1$–$C_4$ alkyl, $C_1$–$C_4$ alkoxy, halosubstituted ($C_1$–$C_6$) alkyl and halosubstituted ($C_1$–$C_6$) alkoxy; n is 4 or 5; and M is hydrogen or a pharmaceutically acceptable cation.

3. A compound according to claim 2 wherein $R^1$ and $R^2$ are each hydrogen and X is oxygen.

4. A compound according to claim 3 wherein Ar is phenyl or monohalosubstituted phenyl; and A is $C_3$–$C_6$ alkylene having one triple bond, and optionally having one $C_1$–$C_4$ alkyl group attached to the chain.

5. A compound according to claim 4 wherein Ar is phenyl or 4-fluorophenyl; and A is —C≡CCH(CH₃)—.

6. A compound according to claim 3 wherein Ar is phenyl or halosubstituted phenyl; and A is $C_3$–$C_6$ alkylene having one double bond, and optionally having one $C_1$–$C_4$ alkylene group attached to the chain.

7. A compound according to claim 3 wherein Ar is phenyl or halosubstituted phenyl; and A is a valence bond or $C_1$–$C_6$ alkylene optionally, having one $C_1$–$C_4$ alkyl group attached to the chain.

8. A compound according to claim 7 wherein Ar is phenyl or 4-fluoro-phenyl; and A is a valence bond or —CH(CH₃)—.

9. A compound according to claim I selected from
(+)-N-[4-cis-3-(4-fluorophenoxy)cyclobutyl}-3-butyn-2-yl-N-hydroxyurea;
(−)-N-[4-cis-3-(4-fluorophenoxy)cyclobutyl}-3-butyn-2-yl-N-hydroxyurea;
(+)-N-[4-trans-3-(4-fluorophenoxy)cyclobutyl}-3-butyn-2-yl-N-hydroxyurea;
(−)-N-[4-trans-3-(4-fluorophenoxy)cyclobutyl}-3-butyn-2-yl-N-hydroxyurea; N-hydroxy-N-(1S,3S)-3-phenoxycyclopentylurea;
(+)-N-[4-{cis-3-(4-chlorophenoxy)cyclobutyl}-3-butyn-2-yl]-N-hydroxyurea;
(−)-N-[4-{cis-3-(4-chlorophenoxy)cyclobutyl}-3-butyn-2-yl]-N-hydroxyurea;
(+)-N-[4-{-cis-3-(2-chloro-4-fluorophenoxy)cyclobutyl}-3-butyn-2-yl]-N -hydroxyurea;
(−)-N-[4-{cis-3-(2-chloro-4-fluorophenoxy)cyclobutyl}-3-butyn-2-yl]-N -hydroxyurea;
(+)-N-[4-{cis-3-(4-fluoro-2-methylphenoxy)cyclobutyl}-3-butyn-2-yl]-N-hydroxyurea; and
(−)-N-[4-{cis-3-(4-fluoro-2-methylphenoxy)cyclobutyl}-3-butyn-2-yl]-N-hydroxyurea.

10. A pharmaceutical composition for the treatment of an inflammatory disease, allergy or cardiovascular disease in a mammalian subject which comprises a therapeutically effective amount of a compound of claim 1 and its pharmaceutically acceptable carrier.

11. A method for the treatment of a medical condition for which a 5-lipoxygenase inhibitor is needed, in a mammalian subject, which comprises administering to said subject a therapeutically effective amount of a compound according to claim 1.

12. A method according to claim 11, wherein the medical condition is an allergic or inflammatory condition.

13. A process for preparing a compound according to claim 1, which comprises reacting a hydroxylamine of the formula

wherein Ar, A, X, and n have the same meanings as defined in claim 1, with either (A) trialkylsilyl isocyanate in a reaction-inert solvent, or (B) gaseous hydrogen chloride and phosgene in a reaction-inert solvent, followed by a compound of the formula $NHR^1R^2$, wherein $R^1$ and $R^2$ have the same meanings as defined in claim 1.

* * * * *